United States Patent [19]

Gabrán

[11] Patent Number: 4,874,379
[45] Date of Patent: Oct. 17, 1989

[54] CANNULA

[75] Inventor: Clas Gabrán, Helsinki, Finland

[73] Assignee: Oy Stille Ab, Helsinki, Finland

[21] Appl. No.: 207,769

[22] Filed: Jun. 15, 1988

[30] Foreign Application Priority Data

Jun. 17, 1987 [FI] Finland .................................. 872707

[51] Int. Cl.⁴ .............................................. A61M 5/00
[52] U.S. Cl. ..................... 604/168; 604/900
[58] Field of Search ................. 604/164–170, 604/900

[56] References Cited

U.S. PATENT DOCUMENTS 4,231,367 11/1980 Rash ..................................... 604/165
4,269,186 5/1981 Loveless et al. ..................... 604/168

Primary Examiner—Dalton L. Truluck
Attorney, Agent, or Firm—Lorusso & Loud

[57] ABSTRACT

The invention is related to a cannula used in medication for infusing liquid and/or giving a medicine injection into a vein, which cannula comprises a hollow body, an indication chamber part that, equipped with a steel needle, is coupled to it, a catheter, and a rear plug. To achieve a cannula that would be more advantageous to handle, the body and the indication chamber part, coupled to each other, are essentially at right angles to each other, in such a way that the indication chamber in said chamber part is in an essentially vertical position, having in its upper part an indicating device, and the chamber part is shaped to be held between the thumb and the forefinger.

5 Claims, 2 Drawing Sheets

CANNULA

FIELD OF THE INVENTION

This invention is related to a cannula used in medication for infusing liquid and/or giving a medicine injection into a vein, which cannula comprises a hollow body, an indication chamber part that, equipped with a steel cannula, is coupled to it, a catheter, and a rear plug.

BACKGROUND OF THE INVENTION

Known cannulae generally comprise a two-piece body, to the front part of which belong wings for fastening the cannula on the patient's skin for instance with adhesive tape, a point of support for the operator's forefinger for handling the cannula (a capped injection valve for medicine injections often serves as such point of support), a flexible catheter through which the liquid is infused or injected into the vein, and fittings (a so-called Luer lock fitting) for the rear plug or for the supply hose of the liquid to be infused.

The rear part of the body consists of a so-called indication chamber that can be uncoupled from the former, which shows the flowing of blood into the cannula and through which the cannula can be deaerated before treatment. At the front of the chamber is also fastened a hollow steel needle, or a steel cannula, with which the vein will be punctured and which part of the body the operator pulls out from the vein and from the cannula hub, leaving the flexible catheter in the vein. The rear part is also provided with a vertical support plate mainly for the thumb.

Cannulae of this kind have several disadvantages. First, the operator's hold mainly between the thumb and the forefinger is not the best possible for giving injections because it easily happens that the steel needle's direction of movement deviates from both the operator's aiming line and his hand's direction of movement, and so practice is needed to find the right puncture point and angle.

Second, the injection valve serving as the forefinger's point of support cannot be shaped more friendly for the operator's hold because usually such valves are of standard make. The smallest cannulae have no room at all for such valves, so it has been necessary to provide them with separate support plates, which increases the cost of such cannulae and eliminates in them the possibility of giving medicaments in the form of injections.

As a third disadvantage could be mentioned that the rear plug of the cannula is usually fastened either on a wing on the cannula's front part or behind the cannula's rear part, that is the indication chamber, in which cases it cannot be removed with the hand that holds the cannula. As the other hand is busy enough, for instance pressing the punctured area while the steel needle is being pulled out, calming down the patient, and so on, to remove the plug from its holder and insert it into the opening is a difficult operation.

SUMMARY OF THE INVENTION

The object of this invention is to create a new kind of cannula with none of the above-mentioned disadvantages. To achieve this, a cannula based on the invention is characterized by that, coupled to each other, the body and the indication chamber part are essentially at right angles to each other, in such a way that the indication chamber in said chamber part is in an essentially vertical position, having in its upper part an indicating device, and by that the chamber part is shaped to be held between the thumb and forefinger.

The most significant advantages of a cannula based on the invention are based on the indication chamber's new design. It provides a better and firmer hold on the cannula because the thumb and the forefinger press between themselves a one-piece indication chamber, and it will be held and taken to the vein in the direction of the arm, the result being that the aiming accuracy and the delicacy of the puncture are optimal. Not only does this cannula concept provide a good hold on the cannula, it also results in a smaller cannula because the usual long indication chamber is not there.

An advantageouso embodiment of the invention is characterized by that the body is equipped with an injection valve. Even with small cannulae, it is often advantageous if there is an injection valve included for dosing medicaments direct into the vein. The construction of a cannula based on the invention makes that possible at least down to Gauge 24.

An advantageous embodiment of the invention is also characterized by that on that surface of the indication chamber part which points toward the catheter are fastening elements for the rear plug. By arranging the plug this way, the convenience of use for a cannula based on the invention is increased because the plug can be removed from the indication chamber part and put in place at the end of the body without the operator's changing his hold. Other advantageous embodiments of the invention are characterized by what is presented below in the patent claims.

BRIEF DESCRIPTION OF THE DRAWING

In the following, the invention is explained in more detail, with reference to the attached drawings, in which.

Figure 1:
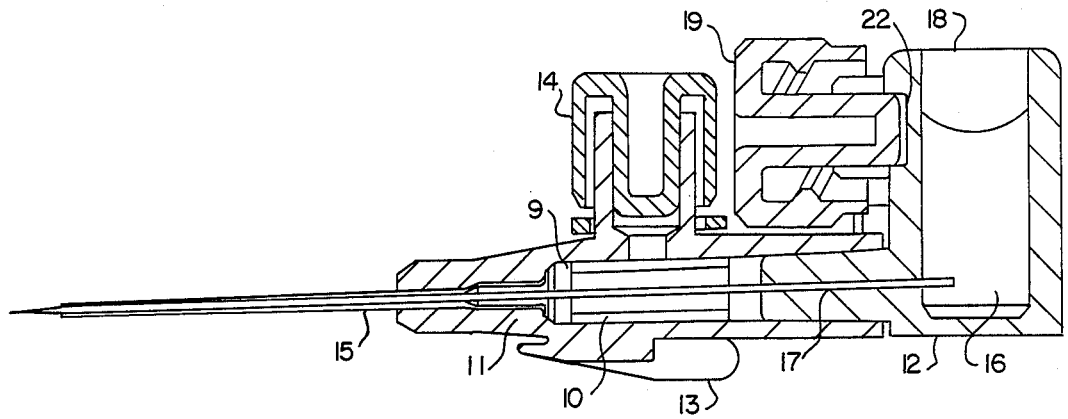
FIG. 1 shows an embodiment of a cannula based on the invention from the side and in section.

The cannulae are shown in all the figures on the scale of about 3:1.

DETAILED DESCRIPTION OF THE PREFERRED EMBODIMENTS

The normal construction and normal method of use of a cannula are explained in the following, with reference to FIG. 3. The cannula comprises a two-piece body, the actual body 1 having wings 3 (see FIG. 2) for fixing the cannula on the patient's skin for instance with adhesive tape, a point of support for the operator's forefinger for handling the cannula (as which point of support often serves a back-pressure injection valve for medicine injections covered with a cap 4), a flexible catheter 5 through which the liquid is infused or injected into the vein, and at the back fittings, or a Luer lock fitting, (not drawn in the figure) for the rear plug 6 or for the supply hose of the liquid to be infused. An alternative place for the plug 6 in known cannulae is often on one of the two wings 3.

The other main component of the cannula consists of an indication chamber part 2 that can be decoupled from the body 1. The indication chamber 7 (drawn with a dashed line) contained in it shows the flow of blood into the cannula, and the cannula can be deaerated through the indication chamber before treatment, for instance through a filter. Attached to the chamber part 2 are also a hollow steel needle, or a steel cannula, (not drawn in the figure) and a vertical support plate 8 mainly for the thumb.

The infusion or injection is done so that the operator grips the cannula with two or three fingers, yet always in such a manner that the thumb rests against the plate 8 and the forefinger is pressed in front of the valve 4 toward the thumb. The wall of the vein is pierced with the needle, and then the operator waits till the indication chamber 7 is filled with blood. After this the body 1 and the chamber part 2 are decoupled by holding the chamber part 2 and thus the needle immobile and at the same time pushing the valve 4, which makes the catheter 5 slide along the needle into the vein. Once the catheter is in the vein, the vein is carefully pressed in front of the catheter's point with a finger and the steel needle is pulled out from the vein with the hand on the chamber part 2. The opening remaining at the back of the body 1 is then closed with a Luer lock plug 6, or an infusion hose is coupled to it. The eventual injection is done in the usual way through the valve 4 situated under the cap 4.

A cannula based on the invention is shown in section in FIG. 1. The body of the cannula comprises an actual body 11, and an indication chamber part 23 which is made of transparent plastic. In a way similar to known canulae, attached to the body 11 are wings 13, a conventional back-pressure injection valve 9 based on the compression of a valve rubber 10 and provided with a protective plug 14, and a catheter 15. In the cannula based on the invention, however, the body 11 and the indication chamber part 12 have been coupled at right angles to each other. To the chamber part 12 belongs an essential vertical indication chamber 16, in the upper part of which there are a filter plug 18 of porous, sintered plastic, and a hollow steel needle 17. The plug 18 lets air pass through but holds back the escape of blood for the time the operator needs for pulling the steel needle 17 from the vein and throwing away the part 12 with the needle.

Figure 2:
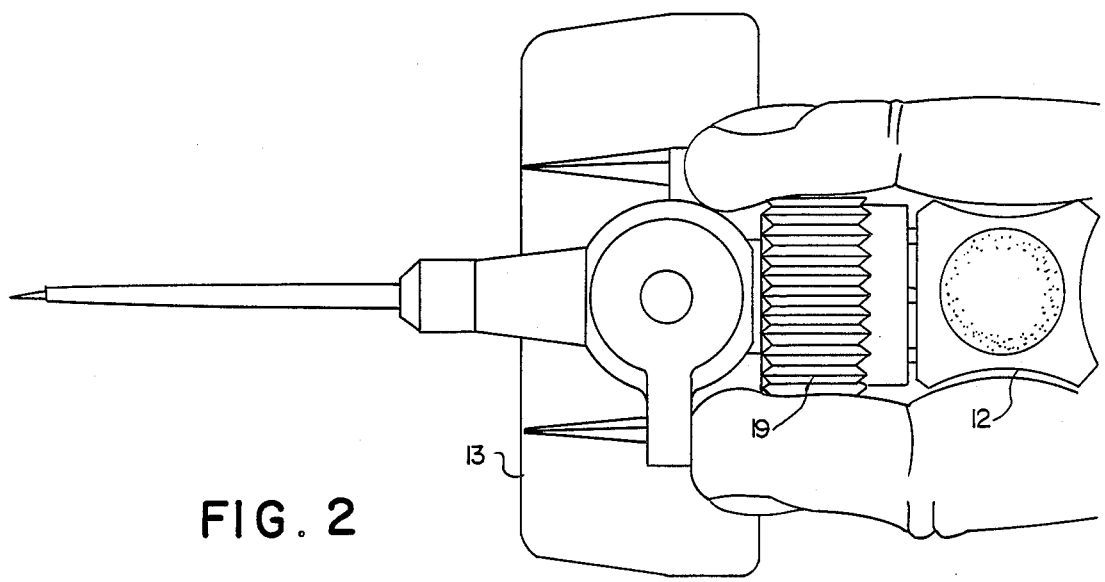
FIG. 2 shows a cannula according to FIG. 1 from above.
Figure 3:
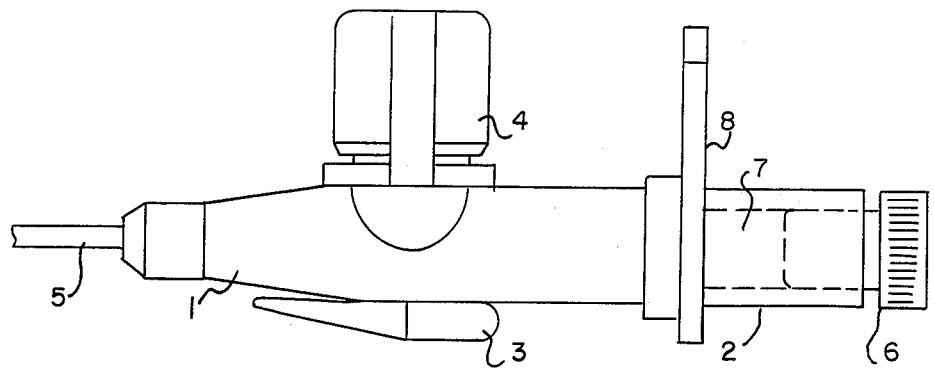
FIG. 3 shows a known cannula from the side.

The rear plug 19 is situated on the body part 12 in such a way that it fills the empty space between the valve plug 14 and the chamber part 12, thus also improving the firmness of the operator's hold (see FIG. 2). The plug 19 cannot drop from the cannula even with careless handling because it has not as much room as would be necessary for it to get totally loose from its holder (which consists for instance of a recess 22 with the plug partially inserted in it) on the wall of the chamber part 12 unless the parts 11 and 12 have been pulled apart.

FIG. 2 shows the cannula in FIG. 1 from above, revealing for instance the shape of the wings 13. Moreover, the concave form of the sides 12 is clearly seen, and the thumb and the forefinger drawn in the figure show that the operator's hold is similar to how one holds a pen.

Figure 4:
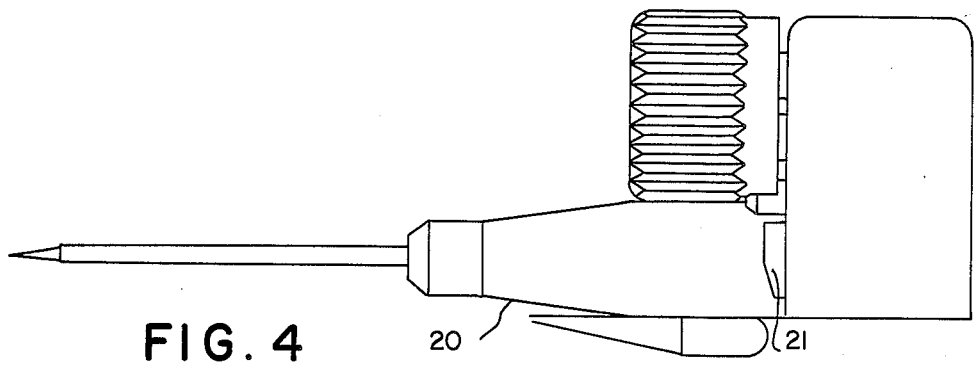
FIG. 4 shows another embodiment of a cannula based on the invention from the side.

A cannula based on the invention is used almost in the same way as what was described in connection with FIG. 3, but the operator's hold on the cannula is as shown in FIG. 2, which means that there is no need to bend or turn fingers or the palm to any particular position or angle. Furthermore, the removal of the plug 19 can be done with the fingers shown in FIG. 2 without changing their hold, in such a way that when the steel needle is pulled from the vein and the operator is holding in his hand the chamber part 12 with the needle, the plug 19 is pushed somewhat apart from the chamber part 12, at which the chamber part 12 drops off and the plug 19 can be turned on its internal Luer thread (see FIG. 1) onto the lugs 21, which are best seen in FIG. 4. The whole operations happens without changing the hold shown in FIG. 2, as a result of which the body 11 of the cannula jerks or shifts as little as possible.

FIG. 4 shows a cannula based on another embodiment of the invention, which has no separate injection valve. So it is only the body 20 that is essentially different from its counterpart, that is body 11, in FIG. 1. Furthermore, the Luer thread 21 for the rear plug 19 or for the connector (not drawn in the figure) of the infusion hose is clearly seen. A cannula corresponding to FIG. 4 is very small and light, and it still has all the advantages of the invention.

It is obvious to a person skilled in the art that the invention is not restricted to the above example, but can be varied within the scope of the following patent claims. So for instance the fastening of the plug 19 to the body part 12 can be based on any fastening elements available in the market, and the shape of the part 12 that facilitates the operator's hold can also be something else than only the concave design of the side surfaces, for instance grooved or rifled surface.

I claim:

1. A cannula for introducing liquid into the vein of a patient comprising:
    a main body defining front and rear openings and a passage therebetween having a first longitudinal axis;
    a catheter projecting out from said front opening and capable of of being inserted into the patient's vein to place the patient's vein into fluid communication with said passage;
    a rear body defining an indicating chamber having a second longitudinal axis and having a male coupling element with an aperture passing therethrough projecting substantially perpendicularly away from said indicating chamber, said male coupling element being removably inserted into said rear opening of said main body coaxially with said first longitudinal axis so that said second longitudinal axis is substantially perpendicular to said first longitudinal axis;
    a hollow steel needle affixed to said rear body and passing through said aperture of said male coupling element, said passage, and said catheter, to be thereby capable of placing said indicating chamber in fluid communication with the patient's vein when said catheter is inserted into the vein; and
    a rear plug detachably affixed to said rear body so that when said male coupling element is withdrawn from said rear opening to separate said rear body from said main body, said rear plug can be detached from said rear body and connected to said main body to cap said rear opening.

2. Cannula according to claim 1, wherein the main body is equipped with an injection valve.

3. Cannula according to claim 1, wherein said rear body has outer surfaces a first of which points toward the catheter and upon which are fastening elements for the rear plug.

4. Cannula according to claim 1, wherein of the outer surfaces of the rear body at least those surfaces that are oriented vertically and face perpendicularly to said first surface are concave in shape.

5. The cannula as set forth in claim 1 wherein said indicating chamber is provided with an indicating device through which the flow of blood into the indicating chamber is readily visible.

* * * * *